(12) United States Patent
Owens

(10) Patent No.: US 6,494,906 B1
(45) Date of Patent: Dec. 17, 2002

(54) STENT FOLD CLIP

(75) Inventor: Timothy R. Owens, Dublin, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 183 days.

(21) Appl. No.: 09/624,721

(22) Filed: Jul. 25, 2000

(51) Int. Cl.[7] ................................................. A61F 2/06
(52) U.S. Cl. ..................................... 623/1.11; 623/1.15
(58) Field of Search ............................. 623/1.11, 1.15, 623/1.16; 606/108, 195

(56) References Cited

U.S. PATENT DOCUMENTS

| | | | | |
|---|---|---|---|---|
| 5,344,426 A | * | 9/1994 | Lau et al. | 606/198 |
| 5,746,745 A | * | 5/1998 | Abele et al. | 606/108 |
| 5,836,965 A | * | 11/1998 | Jendersee et al. | 606/198 |
| 5,913,871 A | * | 6/1999 | Werneth et al. | 606/194 |
| 5,935,135 A | * | 8/1999 | Bramfitt et al. | 606/108 |
| 6,254,608 B1 | * | 7/2001 | Solar | 606/108 |
| 6,258,099 B1 | * | 7/2001 | Mareiro et al. | 606/108 |
| 6,280,412 B1 | * | 8/2001 | Pederson, Jr. et al. | 604/103.07 |

* cited by examiner

*Primary Examiner*—David H. Willse
*Assistant Examiner*—Javier G. Blanco
(74) *Attorney, Agent, or Firm*—Fulwider Patton Lee & Utecht, LLP

(57) ABSTRACT

An apparatus for secure stent delivery where the stent is delivered by a catheter system including a foldable delivery balloon. The apparatus, embodied in a stent with tethering clips, enables the stent and delivery balloon to be mechanically interlocked during delivery of the stent. The tethering clips are coupled to a strut included in the stent and the clips are positionable in a releasable gripping relationship with a fold in the balloon. When the balloon is inflated, the tethering clips are pushed outward and the stent and balloon are no longer interlocked, allowing the stent to be expandable radially by the inflating balloon.

44 Claims, 3 Drawing Sheets

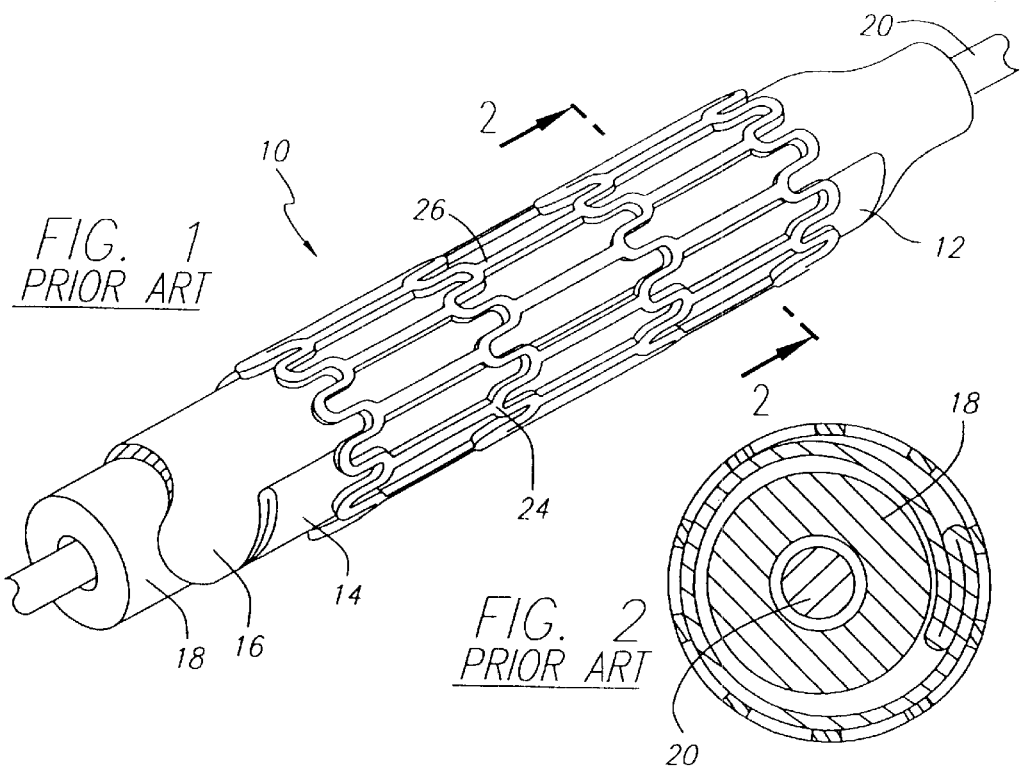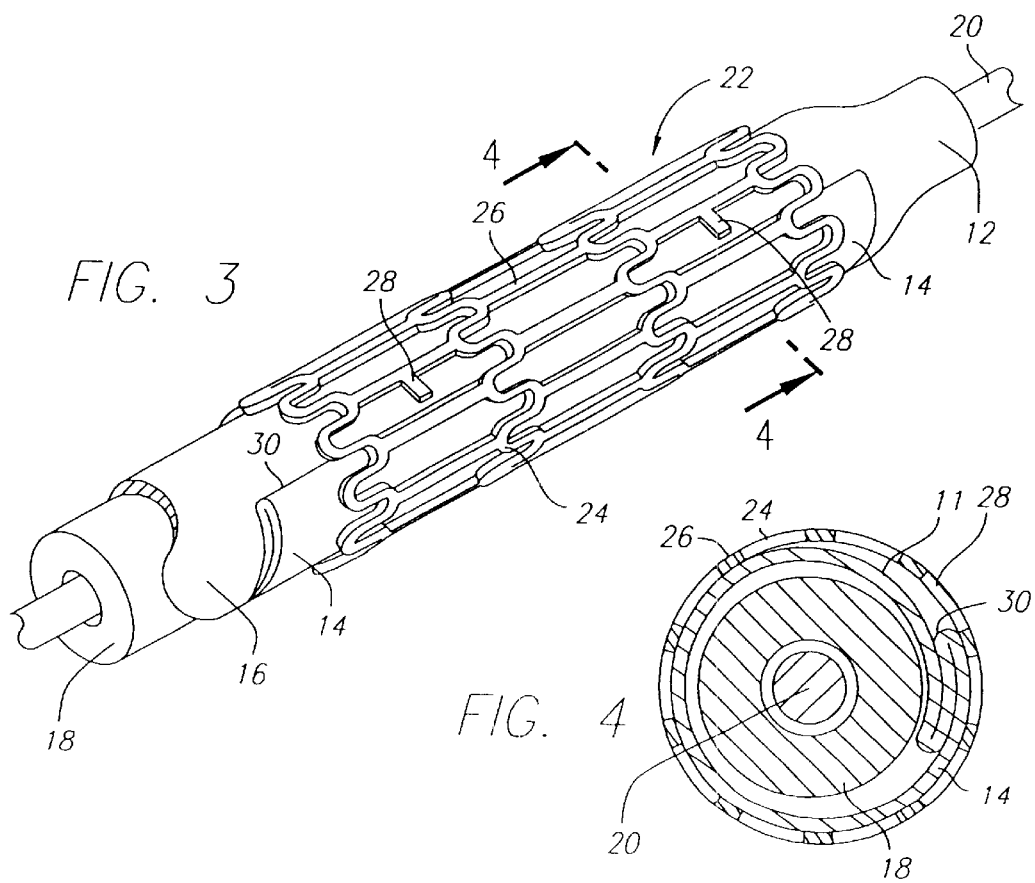

STENT FOLD CLIP

BACKGROUND OF THE INVENTION

The present invention generally relates to stent devices for delivery on foldable delivery balloons and, more particularly, to a stent configured for mounting on a balloon in a releasable gripping relationship.

Angioplasty is a procedure in which a balloon is positioned in an artery at the site of a lesion and expanded to compress the materials at the lesion in order to open the restricted area in the artery. In this procedure, a balloon is formed on one end of a catheter. The catheter is inserted transluminally over a previously placed guide wire to maneuver the balloon through the patient's vessels to the site of the lesion. When the uninflated balloon is properly positioned at the lesion, the balloon is inflated to dilate the restricted area.

In these procedures there may be restenosis, also referred to as recurrent stenosis, of the artery. Restenosis may require another angioplasty procedure, a surgical bypass operation, or some method of repairing or strengthening the area. To reduce the risk of restenosis and strengthen the area, a physician can implant at the treatment area an intravascular prosthesis for maintaining vascular patency, typically called a stent. A stent is a device used to hold tissue in place or to provide support for a graft or tissue joined while healing is taking place. Stents are typically implanted by use of a delivery catheter which is inserted at an easily accessible location and then advanced through the vasculature to the deployment site. The stent is initially maintained in a radially compressed or collapsed state to enable it to be maneuvered through a body lumen. Once in position, the stent is usually deployed either automatically by the removal of a restraint, or actively by the inflation of a balloon about which the stent is carried on the delivery catheter. In reference to balloon catheter stents, a variety of devices are known in the art for use as stents, including coiled wires and wire mesh sleeves in a variety of patterns that are able to be crimped onto a balloon catheter, and that are capable of retaining their expanded form. Typically, the stent is mounted and crimped onto the balloon portion of the catheter, and advanced to a location inside the lumen at the lesion. The balloon is then inflated to expand the stent to a larger diameter to permanently implant it in the artery at the lesion.

As previously mentioned, an attribute of a stent delivery system is its ability to have the stent tightly crimp on the balloon portion during stent delivery. This form of mechanical interlock between the stent and catheter balloon is known as stent security. The objective of stent security is to prevent the stent from moving relative to the balloon during delivery of the stent in the patient's vasculature. Good stent security is important in preventing the stent from separating from the balloon before the delivery system is in a desired anatomical location and to hold the stent in the desired position on the balloon. A stent that is repositioned on a balloon or a stent that is separated from the balloon may cause many adverse complications. One such adverse complication includes deploying the stent in a less than optimal anatomic location. This complication can lead directly to a complete occlusion of an artery. Moreover, if the stent should slide off the delivery catheter prior to expansion, the stent may somewhat block the flow of blood and could require an emergency surgical procedure to recapture the stent.

In the assembly of a stent delivery system, the balloon portion is typically folded around the catheter shaft in a "jelly roll" configuration. The stent is then slid over the folded balloon and squeezed down or "crimped" onto the balloon.

Current stent delivery construction poses certain shortcomings. For example, those arrangements where the balloon is pressed between the stent mesh impose design constraints on the amount of stent material that can be used and on the stent metal pattern. Other methods may result in an increase in the stent delivery system diameter or profile, which in turn increases the risk of clinical complications and can prevent the delivery of the stent to tight, distal lesions.

An improved stent with enhanced security is therefore needed to overcome the problems in the prior art. More particularly, the improved stent should provide a higher degree of safety than conventional stents and should be comparatively inexpensive to manufacture. The present invention satisfies these and other needs.

SUMMARY OF THE INVENTION

Briefly, and in general terms, the present invention provides a new and improved apparatus and method to be used in stent delivery on foldable delivery balloons. More specifically, the apparatus and accompanying method provide a stent configured for mounting on a balloon in a releasable gripping relationship which increases stent retention on the delivery catheter.

In general terms, this invention describes a novel apparatus and method to enhance stent security by incorporating balloon clips on the stent which are adapted to grip the folds which are created when the catheter balloon is initially folded. A critical attribute of a stent delivery system is stent security. In the context of this invention, stent security is achieved through the mechanical interlock between the stent and the catheter balloon. The objective of stent security is to prevent the stent from moving relative to the balloon.

In one aspect of the present invention, the stent device incorporates tethering clips which are adapted to hold the stent on the balloon portion of the delivery catheter. The stent device slides over the balloon which is folded on the delivery catheter. The tethering clips are configured so as to be positionable in a releasable gripping relationship within the folds in the folded balloon. In this configuration, the clips will be gripped by a fold in the balloon as the device is inserted into a patient's vasculature. After the balloon is inserted into the body vessel and properly positioned in the area of treatment, it is inflated. The tethering clips are constructed so they will be released from the folds of the balloon as the balloon inflates to allow the stent to be freely deployed within the body vessel.

In another aspect of the present invention, the stent can include one or more longitudinal struts to which the tethering clips are connected. The clips are carried on their respective ends by the strut to leave a free-end shape which can be placed within the folds of the balloon during manufacture.

The free end of the clip may be in the form of a stop to create frictional resistance between itself and the balloon. This mechanical interlock between the stent and the catheter balloon thus provides increased stent security by resisting movement of the stent relative to the balloon. The stop itself can take many different configurations including a knurled surface, corrugated body, or an enlarged tip. All of these configurations should provide a suitable frictional attachment within the folds of the balloon as the stent is being inserted into a patient's vasculature.

The tethering clips can also be coupled to, and configured on, the stent in a variety of other ways to provide the mechanical interlock between the stent and the balloon. In one aspect of the present invention, the tethering clips are pivotally mounted on the strut so as to enable the clips to be easily rotated into a position to secure the stent to the balloon.

The clips also can be formed from a ductile material. In this instance, the ductility of the clip enables it to be easily orientated for positioning into a balloon fold. After being positioned, the clip's natural resistance to bending performs the mechanical interlock function between the balloon and the stent.

The present invention can be made with a plurality of clips connected to the stent. Each clip can be configured in either of the configurations mentioned above so as to provide a suitable mechanical interlock between the stent and the balloon.

In an accompanying method, an intra-luminal stent including at least one tethering clip is positioned in a fold of a folding delivery balloon. The tethering clips are positioned in the folds so as to releasably hold the stent in position mechanically locked on the balloon. After the stent and balloon are mechanically interlocked, the catheter system is inserted into a patient's vasculature to deliver the stent to a desired deployment location. When the balloon is inflated, clips are released from the balloon fold and the stent continues to expand. At completion of inflation, the balloon is removed and the stent it securely implanted into the patient's body vessel.

These and other features and advantages of the present invention will become apparent from the following detailed description, taken in conjunction with the accompanying drawings, which illustrate, by way of example, the features of the invention.

BRIEF DESCRIPTION OF THE DRAWINGS

FIG. 1 is a perspective view of a prior art stent mounted on a delivery balloon;

FIG. 2 is an enlarged cross-sectional view of the stent shown in FIG. 1;

FIG. 3 is a perspective view of the stent of the present invention depicting tethering clips;

FIG. 4 is an enlarged cross-sectional view of the stent shown in FIG. 3;

DETAILED DESCRIPTION OF THE PREFERRED EMBODIMENTS

Figure 5:
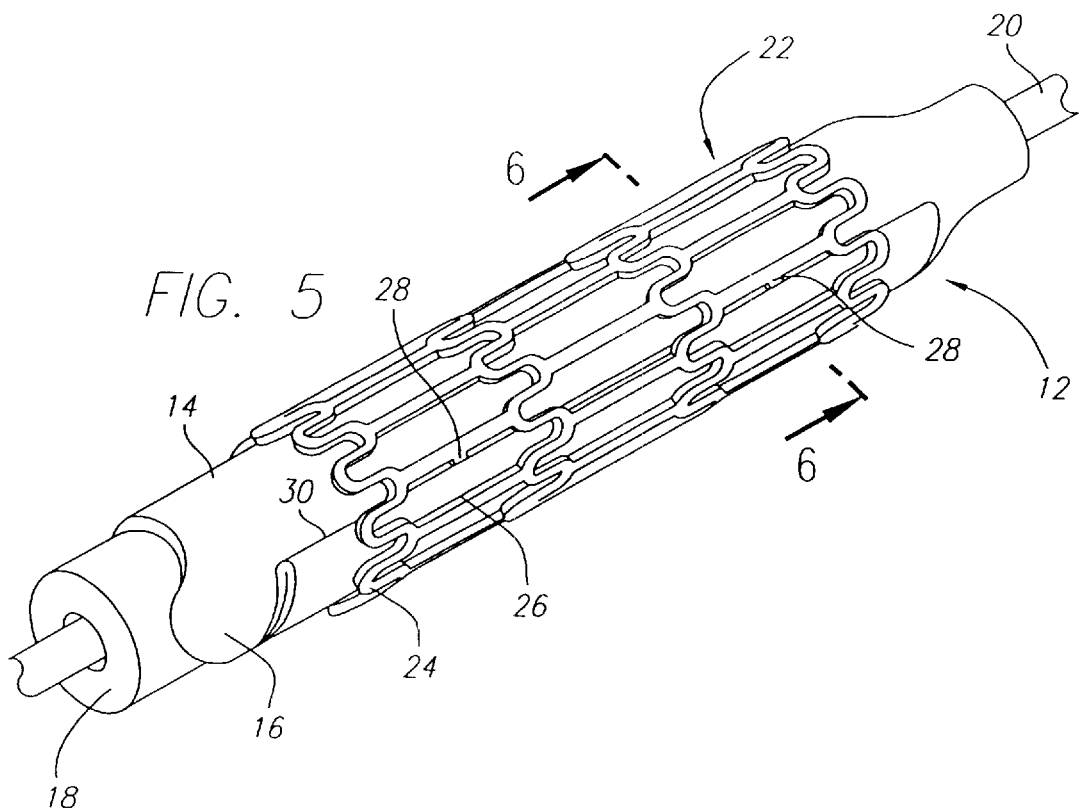
FIG. 5 is a perspective view of the stent shown in FIG. 3 with the clips interlocked.

Referring now to the drawings, in which reference numerals represent like or corresponding elements across the drawings, a prior art stent 10 in shown in FIG. 1 as it is mounted on a delivery catheter at a distal region which includes an expandable member, such as a balloon 14. Typically, the stent is mounted and crimped onto the expandable balloon 14 of the delivery catheter 12, and is advanced to a lesion location within the patient's vasculature. The stent 10 is expanded to a larger diameter by inflation of the balloon 14 to implant the stent in the patient's lumen at the lesion site. Typically, the balloon 14 is pre-wrapped or folded about the catheter shaft in a "jelly roll" configuration which will allow the balloon portion 14 to expand to a fully inflated condition. The delivery catheter 12 includes an outer tubular member 16 which includes the balloon portion 14. An inner tubular member 18 extends coaxially within the outer tubular member 16 to form a composite catheter. An annular space between the outer tubular member 16 and inner tubular member 18 forms a conduit through which inflation fluid can be introduced to inflate the balloon portion 14 of the catheter. As is shown in the figures, the delivery catheter 12 slides along a guide wire 20 in order to reach the target location within the patient's vasculature where the stent is to be implanted.

It should be appreciated that the delivery catheter shown in the present invention is just one of many delivery catheters which can be utilized in accordance with the present invention. Other types of stent delivery catheters having foldable balloon portions can also be utilized with the present invention to increase stent security.

Referring now to FIGS. 3–6, one embodiment of a stent 22 made in accordance with the present invention is shown. FIGS. 3 and 4 show the stent 22 as it is initially mounted on a delivery catheter 12. The stent 22 is made from a number of struts which join together to form the intricate structural pattern which is implanted in the patient's vasculature. In the embodiment shown in FIGS. 3–6, the stent 22 is shown having a number of cylindrical elements 24 which are connected by a number of interconnecting members 26. The cylindrical elements 24 are in the form of a serpentine pattern and are each connected by at least one interconnecting member 26. The serpentine pattern can be made up of a plurality of U-shaped members which allow the expansion forces to be more easily distributed over the cylindrical element 24 as it is being expanded. The number and placement of interconnecting elements 26 can be along the peaks of the undulations as is shown in the figures. However, it should be appreciated that various configurations for the placement of the interconnecting elements are also possible. Also, although the present invention is shown using cylindrical rings or elements and interconnecting members, it should be apparent to one skilled in the art that other structural elements, such a zig zag patterns, coil patterns, and the like can be used to create a composite stenting device. Therefore, the particular pattern of the stent shown in the accompanying figures is just one of numerous configurations which can be utilized in accordance with the present invention.

The stent 22 of the present invention includes a number of tethering clips 28 which are located on certain interconnecting members 26. These tethering clips 28 are shown in a first position in FIGS. 3 and 4 prior to being inserted into the fold 30 which are formed on the balloon portion 14 of the delivery catheter 12. As can be seen in FIGS. 3 and 4, the tethering clips 28 are shown initially flush with the cylindrical elements 24 and its connecting members 26 so that the stent 12 can be slid over the balloon portion 14 of the delivery catheter 12 when the stent 22 is to be secured to the catheter. Although the embodiment shown in FIGS. 3–6 shows the tethering clips 28 formed on certain interconnecting members 26, it is possible to form the clips on the cylindrical elements 24 as well without departing from the spirit and scope of the present invention. Also, it should be appreciated that the tethering clips 28 would be likewise formed on certain struts of a stent which does not necessarily utilize cylindrical elements in combination with interconnecting members to create the composite stenting device. However, the tethering clips placed on strut stents would also act in accordance with the present invention, i.e., to help secure the stent onto the balloon portion of the delivery catheter.

Figure 6:
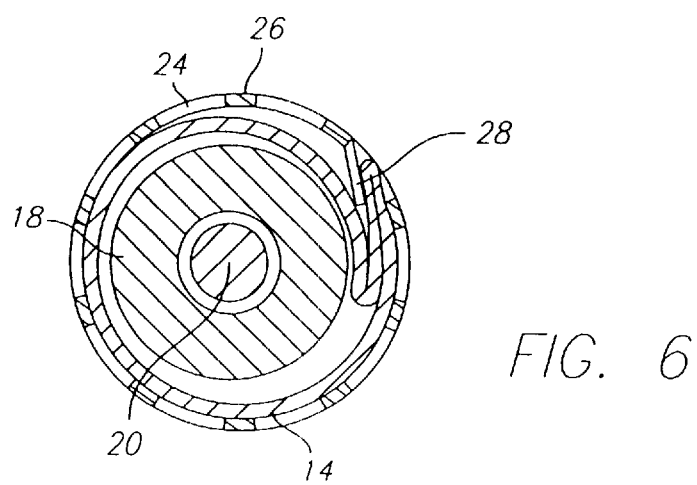
FIG. 6 is an enlarged cross-sectional view of the stent shown in FIG. 5.

As is shown in FIGS. 4 and 6, the balloon portion 14 of the delivery catheter is initially folded in a "jelly roll" like configuration before the stent 22 is placed over the balloon 14. It should be appreciated that only one fold 30 is shown in the balloon portion 14, as can be seen in FIGS. 4 and 6. However, many more fold lines could also be created when the balloon portion is initially folded. FIGS. 4 and 6 are simply shown with a single fold line to more easily show the placement of the clips within the fold. However, it should be appreciated by those skilled in the art that additional tethering clips 28 could be placed at other locations along the struts of the stent 22 to fit in other fold lines which could be created on the balloon portion as well to further enhance the security of the stent onto the balloon.

Referring now to FIGS. 5 and 6, the tethering clips are configured so as to be positionable in a releasable gripping relationship within the fold line 30 of the balloon 14. In these figures, the clips can be formed from a ductile material which allows the clips to be easily bent and thus positioned within the balloon fold 30. The cross-section of the clip which bends is appropriately sized large enough so that it can be bent and placed within the balloon fold 30 without breaking. The cross-section must also be sized small enough so that the resistance to bending is not higher than the amount of force the balloon is capable of placing on the clip when the stent is being deployed. As can be seen in FIGS. 5 and 6, the tethering clip has been rotated to be substantially perpendicular to the longitudinal stent axis which is created by the composite strut pattern. The clips are also bent downward into the cylindrical opening which is formed by the struts of the stent in order to replace within the fold 30 of the balloon portion 14. It should be appreciated that as the balloon portion 14 starts to expand, the folds will start to disappear which will cause the tethering clips 28 to be released from their hold. As the balloon continues to inflate, the tethering clips 28 will be bent back upward flush with the remaining struts of the stent so that when the stent is fully expanded, there should be no clip extending into the internal cylindrical opening formed by the stent. As a result, there should be no protruding edges which could cause a disruption in the normal blood flowing through the stent once it is implanted in the patient's vasculature.

Referring specially now to FIG. 6, the fold line 30 of the balloon portion 14 readily receives the clips 28. With the free extremity of the clips securely encompassed by the fold portion of the balloon, the stent and delivery balloon are securely held together. This secure attachment between the two pieces insures that the stent will not separate from the balloon which would otherwise cause possible complications when it is being delivered through the patient's vasculature. After the balloon and stent are positioned in the target location, the balloon can then be inflated which will allow the tethering clips 28 to release from the fold line 30 and allow the stent to expand to conform to the patient's lumen. The balloon can then be deflated and withdrawn from the patient, leaving the stent implanted in the patient's vasculature.

It should be appreciated that the tethering clips can be formed in almost any manner and from almost any material so long as the clips provide sufficient frictional resistance between the clip and balloon. Frictional resistance must be great enough to prevent the balloon from separating from the stent while being inserted into the patient's vasculature.

Figure 7:
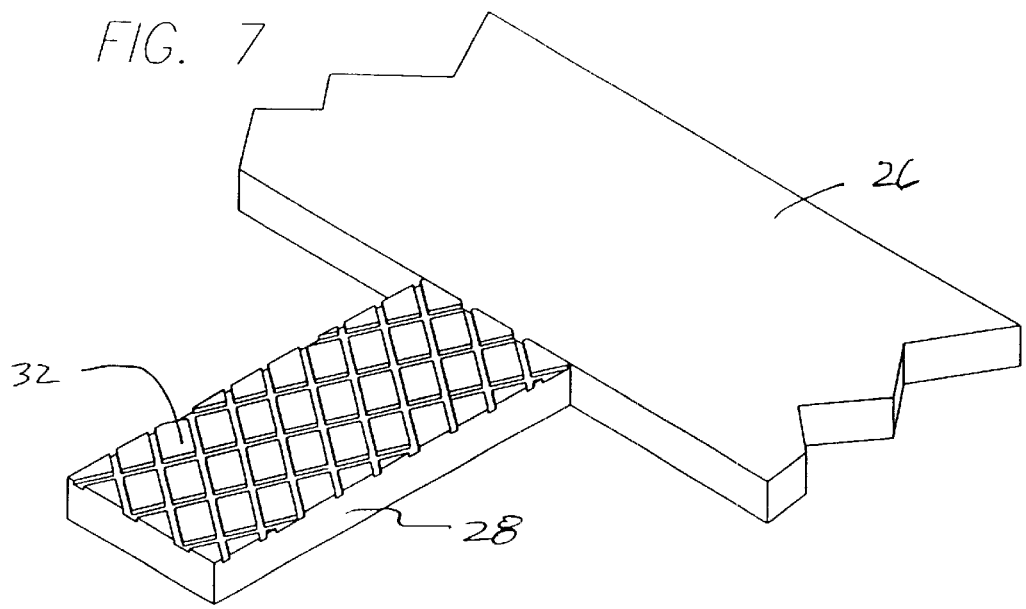
FIG. 7 is an enlarged prospective view of one embodiment of a tethering clip made in accordance with the present invention.
Figure 8:
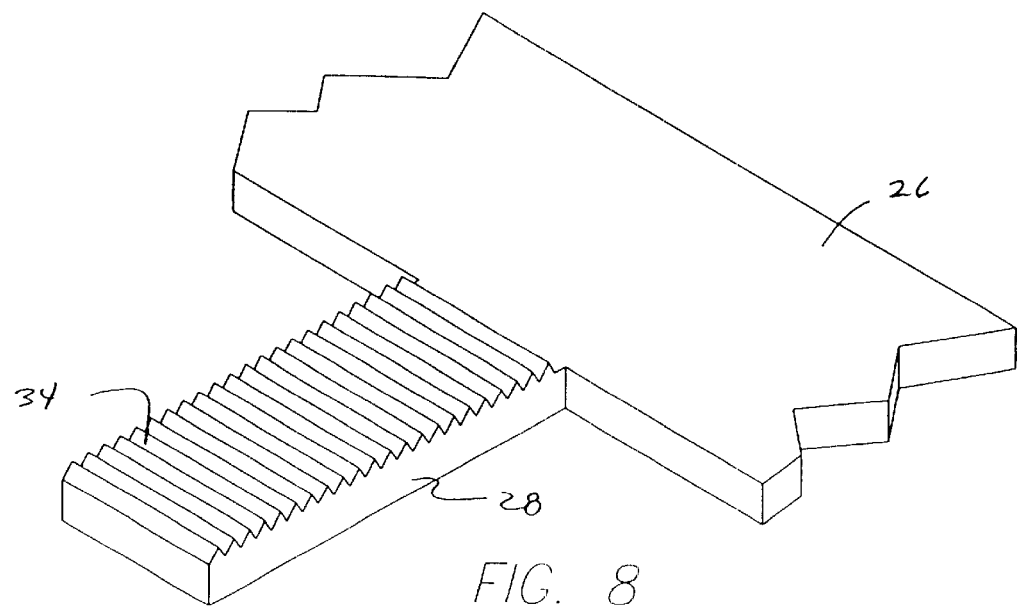
FIG. 8 is an enlarged prospective view of another embodiment of a tethering clip made in accordance with the present invention.

The geometry of the tethering clip 28 itself can be made in as many different configurations and may include a knurled surface 32 (FIG. 7) or, a corrugated surface 34 (FIG. 8), for example. Additionally, the free end of the clip can be made larger than the end which is attached directly to the strut of the stent. These configurations provide for increased resistance which may be necessary which will enhance the security of the stent on the balloon as it is being placed within the patient's vasculature.

The number of tethering clips can also be varied as necessary. If design constraints dictate, a stent with only one tethering tab could also be made without departing from the scope of the present invention if the frictional resistance between the balloon and the clip is sufficiently high to hold both securely together as they are being inserted into the patient. As mentioned above, the number of clips and location of clips can also be varied for the same reason. Likewise, the balloon portion of the catheter can be folded to have more than one fold line which allows the use of additional tethering clips at strategic locations along the stent to better secure the stent onto the delivery catheter. Additional rows of adjacent clips can be placed along the struts to fit in other balloon folds as well.

Radiopaque clips can also be utilized in accordance with the present invention. By utilizing clips which have increased radiopacity, a physician could more easily locate the stent on a fluoroscope or other imaging instruments when positioning the delivery catheter within the patient's vasculature. Moreover, the physician will be able to discern when the stent has been fully deployed by viewing the position of the tethering clips. If the clips are clearly viewable under radiopaque observation, the stent should be fully implanted into the vessel wall. If the clips are less visible, it may indicate to the physician that the stent is not fully deployed.

While the embodiment shown in FIGS. 3–6 is shown with tethering clips that can be bent outward to a 90° angle with the longitudinal stent axis, it is possible to initially form the tethering clip in a 90° relationship with the longitudinal stent axis so that the clips need only to be pushed down into the balloon fold in order to secure the stent on the delivery catheter. Other variations and configurations of the tethering clip 28 can also be made without departing from the spirit and scope of the present invention.

A stent made in accordance with the present invention can be formed from conventional methods such as by using a laser to cut a precise pattern into a thin-walled cylindrical tubing. In this particular method, thin-walled tubular member is cut by a machine-controlled laser which removes portions of the tubing in a desired pattern for the stent, leaving a relatively untouched portion of the metallic tubing which cooperates to form the stent. The laser's cutting pattern is programmed so that to form tethering clips when it is cutting the stent. The tethering clips are therefore formed with the same diameter as the stent so that the clips are flush with the stent, i.e., they do not protrude either into or out of the stent when it is first manufactured. By producing the improved stent in this manner, the cost difference between the improved stent of the present invention and conventional stents is likely to be minimal. Further details on how a stent can be cut by a laser are found in U.S. Pat. No. 5,759,192 (Saunders) and U.S. Pat. No. 5,780,807 (Saunders), which have been assigned to Advanced Cardiovascular Systems, Inc. Similar techniques can be used to form the stent and tethering clips in accordance with the present invention.

The tethering clips can also be added to the stent after the stent is formed. In this aspect of the invention, the clips are coupled to the struts at strategic locations utilizing well-known types of welding, such as brazing and soldering which are well-known in the art. The tethering clips can be pivotally mounted onto the struts of the stent so as to enable the stent to be easily rotated or tilted into position to secure the stent to the balloon portion of the delivery catheter.

A stent made in accordance with the present invention can be made form conventional materials such as stainless steel and tantalum which are well-known in the art. By melding or soldering the clip to the stent, different materials could be utilized for the clips, i.e., a more radiopaque material, to provide the enhanced securing features of the present invention while providing added visualization of the stent under fluoroscopy or other imaging instrumentation.

While a particular form the invention has been illustrated and described, it would be apparent to those skilled in the art that various modifications can be made without departing from the spirit and the scope of the present invention. More particularly, the present invention can be adapted toward numerous conventional stents. In this regard, the tethering clips of the present invention can be attached and adapted to stents in any practical manner. This includes forming the tethering clips as part of the stent or bonding or connecting the tethering clips after the stent has been formed. Accordingly, it is not intended that the invention be limited except by the appended claims.

What is claimed is:

1. A stent for implanting in a body lumen and deliverable on a delivery catheter having an inflatable balloon portion for expanding the stent, comprising:
   a plurality of adjacent struts defining a tubular, radially expandable body which is adapted to expand from a collapsed position to an expanded position in the body lumen; and
   a tethering clip attached to a strut and positionable in a releasable gripping relationship within a fold created when the balloon portion of the delivery catheter is folded in a collapsed position, the clip being adapted to releasably grip the balloon portion to hold the stent on the balloon portion.

2. The stent of claim 1, wherein:
   the clip is elongated, connected at one end to a strut and having at its free end an enlarged transverse cross-section.

3. The stent of claim 1, wherein:
   the clip includes one end connected to a strut and a free end forming a stop so as to create a frictional resistance from withdrawal of the stent from the balloon portion.

4. The stent of claim 3, wherein:
   the free end is formed with knurls for increasing frictional resistance.

5. The stent of claim 3, wherein:
   the free end is formed with corrugations for increasing frictional resistance.

6. The stent of claim 3, wherein:
   the free end is formed with an enlarged cross-section.

7. The stent of claim 1, wherein:
   the clip is pivotally mounted on the strut.

8. The stent of claim 1, wherein:
   the clip is formed from a ductile material.

9. The stent of claim 1, wherein:
   the clip is movably mounted to the strut.

10. The stent of claim 1, further including:
    a plurality of clips connected to the struts.

11. The stent of claim 10, wherein:
    the plurality of clips align substantially adjacent to each other in a longitudinal row.

12. The stent of claim 1, wherein:
    a row of clips are attached to the struts in a substantially straight line arrangement.

13. The stent of claim 12, further including
    a second row of adjacent tethering clips which are attached to the struts and are positionable in a releaseable gripping relationship with a fold formed on the balloon portion of the delivery catheter.

14. The stent of claim 1, wherein:
    the tethering clip is formed from the same material which forms the struts.

15. The stent of claim 1, wherein:
    the tethering clip is made from material which is different from the material which makes up the struts.

16. The stent of claim 15, wherein:
    the material which is used to make the tethering clip has a higher radiopacity that the material which is used to make the struts.

17. The stent of claim 1, wherein:
    the struts are arranged along a longitudinal stent axis to form a generally tubular, regularly expandable body; and
    the tethering clip extends from a strut at an angle which is perpendicular to the longitudinal stent axis and is positionable in a releaseable gripping relationship with the fold formed on the balloon portion of the delivery catheter.

18. A stent for implanting in a body lumen and deliverable on a delivery catheter having an inflatable balloon portion for expanding the stent, comprising:
    a plurality of adjacent struts defining a tubular, radially expandable body which is adapted to expand from a collapsed position to an expanded position in the body lumen; and
    a plurality of tethering clips attached to the struts and positionable in a releasable gripping relationship within a fold created on the balloon portion of the delivery catheter when the balloon portion is folded in a collapsed position to releasably grip the balloon fold to hold the stent on the balloon portion.

19. The stent of claim 18, wherein:
    a plurality tethering clips are arranged along the struts in a substantially straight line arrangement.

20. The stent of claim 18, wherein:
    the plurality of tethering clips are arranged in a pair of rows which are arranged along the struts in a substantially straight line arrangement.

21. The stent of claim 18, wherein:
    the clips are pivotally mounted on the struts.

22. The stent of claim 18, wherein:
    the clips are formed from a ductile material.

23. The stent of claim 18, wherein:
    the tethering clips are formed from the same material which forms the struts.

24. The stent of claim 18, wherein:

the tethering clips are made from material which is different from the material which makes up the struts.

25. The stent of claim 24, wherein;

the material used to make up the tethering clips has a higher radiopacity than the material which is used to make the struts.

26. The stent of claim 18, wherein:

the clips are formed with knurls for increasing frictional resistance.

27. The stent of claim 18, wherein:

the clips are formed with corrugations for increasing frictional resistance.

28. The stent of claim 18, wherein:

the clips are formed with an enlarged cross-section.

29. A method of securing an intra-luminal stent onto a stent delivery catheter having an inflatable balloon portion, including:

selecting a stent having a tethering clip projecting therefrom;

folding an inflatable balloon on a stent delivery catheter to form at least one fold therein; and positioning the clip in the balloon fold to releasably hold the stent in position on the folded balloon.

30. The method of claim 29, further including:

inserting the delivery catheter in a patient's lumen and inflating the balloon to release the clip from the balloon fold.

31. The method of claim 29, further including:

frictionally holding the clip within the fold.

32. The method of claim 29, further including:

inflating the balloon to unfold the balloon.

33. The method of claim 29, further including:

introducing the stent as mounted on the balloon into a vessel lumen.

34. The method of claim 33, further including:

inflating the balloon to release the clip from the balloon fold and to expand the stent.

35. The method of claim 29, wherein:

the step of selecting the stent includes selecting a stent with a clip connected on one of the struts which form the composite stent.

36. A stent for implanting in a body lumen and deliverable on a delivery catheter having an inflatable balloon portion for expanding the stent, comprising:

a plurality of adjacent struts defining a tubular, radially expandable body which is adapted to expand from a collapsed position to an expanded position in the body lumen; and a tethering clip attached to a strut and positionable in a releasable gripping relationship within a fold formed on the balloon portion of the delivery catheter when placed in the collapsed position to releasably grip the balloon to hold the stent on the balloon portion, the clip having one end connected to a strut and a free end forming a stop to create a frictional resistance from withdrawal of the stent from the balloon portion.

37. The stent of claim 36, wherein:

the clip is formed with knurls for increasing frictional resistance.

38. The stent of claim 36, wherein:

the clip is formed with corrugations for increasing frictional resistance.

39. The stent of claim 36, wherein:

the clip is formed with an enlarged cross-section.

40. A stent for implanting in a body lumen and deliverable on a delivery catheter having an inflatable balloon portion for expanding the stent, comprising:

a plurality of adjacent struts defining a tubular, radially expandable body which is adapted to expand from a collapsed position to an expanded position in the body lumen;

a row of tethering clips attached to the struts in a substantially straight line arrangement and positionable in a releasable gripping relationship within a fold formed on the balloon portion of the delivery catheter when placed in the collapsed position to releasably grip the balloon to hold the stent on the balloon portion; and a second row of adjacent tethering clips attached to the struts and positionable in a releaseable gripping relationship with a fold formed on the balloon portion of the delivery catheter.

41. A stent for implanting in a body lumen and deliverable on a delivery catheter having an inflatable balloon portion for expanding the stent, comprising:

a plurality of adjacent struts defining a tubular, radially expandable body which is adapted to expand from a collapsed position to an expanded position in the body lumen; and a tethering clip attached to a strut and positionable in a releasable gripping relationship within a fold formed on the balloon portion of the delivery catheter when placed in the collapsed position to releasably grip the balloon to hold the struts on the balloon portion, the tethering clip being made from material which is different from the material making up the struts.

42. The stent of claim 41, wherein:

the material used to make the tethering clip has a higher radiopacity that the material making up the struts.

43. A stent for implanting in a body lumen and deliverable on a delivery catheter having an inflatable balloon portion for expanding the stent, comprising:

a plurality of adjacent struts defining a tubular, radially expandable body which is adapted to expand from a collapsed position to an expanded position in the body lumen; and a plurality of tethering clips attached to the struts and positionable in a releasable gripping relationship within a fold formed on the balloon portion of the delivery catheter when placed in the collapsed position to releasably grip the balloon to hold the struts on the balloon portion, the tethering clips being made from material which is different from the material making up the struts.

44. The stent of claim 43, wherein:

the material used to make the tethering clips has a higher radiopacity that the material making up the struts.

* * * * *